United States Patent
Segal et al.

(10) Patent No.: US 12,029,759 B2
(45) Date of Patent: Jul. 9, 2024

(54) COMPOSITIONS AND METHODS FOR TREATING NEUROLOGICAL DISORDERS

(71) Applicant: THE REGENTS OF THE UNIVERSITY OF MICHIGAN, Ann Arbor, MI (US)

(72) Inventors: Benjamin M. Segal, Ann Arbor, MI (US); Andrew Sas, Ann Arbor, MI (US); Kevin Carbajal, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 752 days.

(21) Appl. No.: 16/965,816

(22) PCT Filed: Jan. 31, 2019

(86) PCT No.: PCT/US2019/016027
§ 371 (c)(1),
(2) Date: Jul. 29, 2020

(87) PCT Pub. No.: WO2019/152636
PCT Pub. Date: Aug. 8, 2019

(65) Prior Publication Data
US 2021/0113611 A1    Apr. 22, 2021

Related U.S. Application Data

(60) Provisional application No. 62/624,444, filed on Jan. 31, 2018.

(51) Int. Cl.
*A61K 35/15* (2015.01)
*C12N 5/0787* (2010.01)

(52) U.S. Cl.
CPC ............ *A61K 35/15* (2013.01); *C12N 5/0642* (2013.01); *C12N 2500/34* (2013.01); *C12N 2501/105* (2013.01); *C12N 2501/13* (2013.01); *C12N 2501/15* (2013.01)

(58) Field of Classification Search
None
See application file for complete search history.

(56) References Cited

U.S. PATENT DOCUMENTS

| | | | |
|---|---|---|---|
| 2005/0049196 A1* | 3/2005 | Hutchinson | A61K 38/185 514/8.4 |
| 2014/0315805 A1* | 10/2014 | Carmichael | A61P 7/06 514/423 |
| 2016/0015786 A1 | 1/2016 | Levesque et al. | |

FOREIGN PATENT DOCUMENTS

| | | |
|---|---|---|
| WO | 2017/040374 A1 | 3/2017 |
| WO | 2018/187786 A1 | 11/2018 |

OTHER PUBLICATIONS

Sas et al., Nature Immunology vol. 21, pp. 1496-1505 (2020) (Year: 2020).*
Baldwin, et al., "Neuroinflammation Triggered by b-glucan/dectin-1 Signaling Enables CNS Axon Regeneration," Proceedings of the National Academy of Sciences of the United States of America, vol. 112, Issue 8 (2015), pp. 2581-2586.
Frazer, et al., "Enhanced Neutrophil Longevity and Recruitment Contribute to the Severity of Oviduct Pathology during Chlamydia muridarum Infection," Infection and Immunity, vol. 79, No. 10 (2011), pp. 4029-4041.
Written Opinion and International Search Report, International Application No. PCT/US2019/016027, mailed Jun. 10, 2019.

* cited by examiner

*Primary Examiner* — Daniel C Gamett
(74) *Attorney, Agent, or Firm* — Thomas | Horstemeyer, LLP (57) ABSTRACT

Provided herein are compositions and methods for treating neurological disorders. In particular, provided herein are neutrophils that rescue damaged neurons, methods of making such neutrophils, and methods of promoting generation of such neutrophils in vivo.

13 Claims, 11 Drawing Sheets

COMPOSITIONS AND METHODS FOR TREATING NEUROLOGICAL DISORDERS

This application is a national phase application under 35 U.S.C. § 371 of PCT International Application No. PCT/US2019/016027, filed Jan. 31, 2019, which claims the benefit of U.S. provisional application Ser. No. 62/624,444, filed Jan. 31, 2018, which are incorporated herein by reference in their entireties.

STATEMENT REGARDING FEDERALLY SPONSORED RESEARCH OR DEVELOPMENT

This invention was made with government support under EY028350 and EY029159 awarded by the National Institutes of Health. The government has certain rights in the invention.

FIELD

Provided herein are compositions and methods for treating neurological disorders. In particular, provided herein are neutrophils that rescue damaged neurons, methods of making such neutrophils, and methods of promoting generation of such neutrophils in vivo.

BACKGROUND

Axonal injury is a major cause of chronic and progressive disability in a wide range of neurological disorders. It has been recognized as a key predictor of outcome in CNS infections (AIDS), early stage Alzheimer's disease and subcortical ischemia. Approximately half of all cases of severe head trauma are characterized by acute shearing of axons. Axonal transection is also a cardinal pathological feature of Multiple Sclerosis (MS). In both traumatic brain injury (TBI) and MS, axonal pathology leads to Wallerian degeneration and correlates strongly with loss of function. Poor clinical outcomes in all of these neurological conditions are due, in large part, to the limited regenerative capacity of adult CNS neurons.

There is a dire need to develop therapeutic interventions that overcome barriers to repair in the adult CNS, promote axonal regrowth, and mitigate, or even reverse, disability.

SUMMARY

Provided herein are compositions and methods for treating neurological disorders. In particular, provided herein are neutrophils that rescue damaged neurons, methods of making such neutrophils, and methods of promoting generation of such neutrophils in vivo.

Described herein is a subset of myeloid cells that stimulate the regeneration of severed axons and rescue damaged neurons from cell death. These cells express the neutrophil marker Ly6G (though at lower levels than conventional mature neutrophils), as well as the monocyte associated marker CD14. They bear ring form nuclei and express high levels of transcripts encoding arginase-1 and the interleukin (IL)-4 receptor alpha chain. They can be generated in vitro from bone marrow neutrophils by polarization with a cocktail including recombinant IL-4 and granulocyte-colony stimulating factor (G-CSF). To illustrate their function, adoptive transfer of the Ly6G$^{low}$CD14+ cells into the eyes of mice subjected to optic nerve crush injury induces axonal regeneration in vivo. Furthermore, conditioned media harvested from cultures of the Ly6G$^{low}$CD14+ cells directly stimulated neurite outgrowth of explanted dorsal root ganglia neurons or retinal ganglion cells in vitro. In addition, nerve growth factor (NGF), insulin-like growth factor 1 (IGF-1) and transforming growth factor (TGFβ) were identified as components of the conditioned media that are responsible for its pro-regenerative effects. Intraocular injection of an immature human neutrophil cell line that shares characteristics with the murine Ly6G$^{low}$CD14+ cells was sufficient to induce the regeneration of axons in the crushed optic nerves of immuno-incompetent mice. In addition, further provided are drugs that promote the accumulation/differentiation of Ly6G$^{low}$CD14+ cells or their human counterparts at sites of neuronal loss and/or axonopathy, or that simulate their pro-regenerative functions, for use in reversing deficits in individuals suffering from a spectrum of neurological disorders, including traumatic brain or spinal cord injury, amyotrophic lateral sclerosis (ALS), stroke, neurodegenerative diseases (such as Alzheimer's disease), optic neuritis and multiple sclerosis. Such interventions are also beneficial in glaucoma and ischemic optic neuropathy. In some embodiments, reparative myeloid cells are used as an autologous cell to prevent neuronal loss and stimulate axonal regeneration in individuals suffering from such disorders.

For example, in some embodiments, provided herein is a method of studying, treating or preventing a neurological disorder, comprising: administering a plurality of Ly6G$^{low}$CD14$^+$ neutrophils or a secreted product thereof (e.g., one or more of NGF, IGF-1, or TGFβ) to a subject diagnosed with or at risk of a neurological disorder under conditions such that the neurological disorder is treated or prevented. In some embodiments, the secreted product is conditioned media harvested from cultures of the neutrophils. In some embodiments, the administering results in one or more outcomes selected from, for example, axonal regeneration, neurite outgrowth, or regeneration of severed axons. In some embodiments, the administering induces expression of a factor selected from, for example, granulocyte colony-stimulating factor (G-CSF), interleukin 6 (IL-6), C-X-C motif chemokine 10 (CXCL10), C-C motif chemokine ligand 2 (CCL2), or vascular endothelial growth factor alpha (VEGFα). In some embodiments, the administering comprises administering locally to an area affected by the neurological disorder (e.g., the eye, the spinal cord, the CNS, or the brain). In some embodiments, the administering comprises systemic administration. In some embodiments, the Ly6G$^{low}$CD14$^+$ neutrophils are mobilized from bone marrow as mature Ly6G$^{low}$CD14$^+$ neutrophils or isolated from bone marrow as immature neutrophils and differentiated in vitro. In some embodiments, differentiating in vitro comprises contacting neutrophils with TGFβ, curdlan, and/or HIF-1α stabilizing agents. In some embodiments, the stabilizing agent is a prolyl hydroxylase inhibitor. In some embodiments, the Ly6G$^{low}$CD14$^+$ neutrophils are human. The present disclosure is not limited to particular neurological disorders. Examples include, but are not limited to, multiple sclerosis, spinal cord injury including traumatic spinal cord injury, ALS, optic neuritis, neurodegenerative disease (e.g., Alzheimer's disease), traumatic brain injury, central nervous system infection, or severe head trauma.

Further embodiments provide a method of treating or preventing a neurological disorder, comprising: administering an agent that induces in vivo generation of Ly6G$^{low}$CD14$^+$ neutrophils to a subject diagnosed with or at risk of a neurological disorder under conditions such that the neurological disorder is treated or prevented.

Additional embodiments provide a method of obtaining Ly6G$^{low}$CD14$^+$ neutrophils, comprising: a) isolating immature neutrophils from a subject; and b) contacting said immature neutrophils with one or more agents that induce differentiation into Ly6G$^{low}$CD14$^+$ neutrophils. In some embodiments, the immature neutrophils are obtained from blood or bone marrow of said subject. In some embodiments, the method further comprises the step of administering the Ly6G$^{low}$CD14$^+$ neutrophils to a subject diagnosed with or at risk of a neurological disorder. In some embodiments, the subject diagnosed with or at risk of a neurological disorder is the same or a different subject than the subject that the immature neutrophils are isolated from. In some embodiments, the subject is a human.

Yet other embodiments, the present disclosure provides a composition, kit, or system, comprising: a plurality of Ly6G$^{low}$CD14$^+$ neutrophils. In some embodiments, the composition, kit, or system further comprises a pharmaceutically acceptable carrier.

Additional embodiments are described herein.

DESCRIPTION OF THE FIGURES

FIG. 7 shows recombinant IGF1 and NGF promote RGC axon regeneration in vivo. Conversely i.o. administration of neutralizing antibodies to IGF1 and NGF prevent Ly6G$^{low}$ neutrophil mediated RGC axon regeneration in vivo. (A) Recombinant IGF1 and/or NGF were administered on day 0 and 3 post-ONC. 14 days later, the densities of regenerating axons were measured at serial distances from the crush site (n=6-8 nerves in each group) *p<0.05, **p<0.01 compared to rIGF, #p<0.05, ##p<0.01 compared to rNGF. (B) Neutralizing antibodies against IGF land/or NGF were administered i.o. combined with Ly6G$^{low}$ neutrophils on days 0 and 3 post-ONC. Axon densities were measured in optic nerves harvested on day 14 (n=12-16 nerves in each group). *p<0.05, p<0.01 *p<0.001 compared to αIGF1+αNGF, #p<0.05, ##p<0.01 compared to αNGF.+p<0.05++p<0.01 compared to αIGF1. (C) Retinal whole mounts harvested from the groups described in (B) were stained with antibodies against the RGC marker, brn3a, for quantification of neuronal densities. Representative whole mount images are shown in the panels on the left side of the figure (n=6-8 retinas in each group). *p<0.05 compared to αIGF1+αNGF, #p<0.05 compared to αNGF, +p<0.05 compared to αIGF1.

DEFINITIONS

To facilitate an understanding of the present invention, a number of terms and phrases are defined below:

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., neurological disorder). Test compounds comprise both known and potential therapeutic compounds. A test compound can be determined to be therapeutic by screening using the screening methods of the present disclosure.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, and industrial samples. Such examples are not however to be construed as limiting the sample types applicable to the present disclosure.

As used herein, the term "effective amount" refers to the amount of an agent (e.g., an agent described herein) sufficient to effect beneficial or desired results. An effective amount can be administered in one or more administrations, applications or dosages and is not limited to or intended to be limited to a particular formulation or administration route.

As used herein, the term "pharmaceutical composition" refers to the combination of an active agent with a carrier, inert or active, making the composition especially suitable for diagnostic or therapeutic use in vivo, or ex vivo.

As used herein, the term "toxic" refers to any detrimental or harmful effects on a cell or tissue as compared to the same cell or tissue prior to the administration of the toxicant.

As used herein, the term "subject" refers to organisms to be treated by the methods of the present disclosure. Such organisms preferably include, but are not limited to, mammals (e.g., murines, simians, equines, bovines, porcines, canines, felines, and the like), and most preferably includes humans. In the context of the invention, the term "subject" generally refers to an individual who will receive or who has received treatment (e.g., administration of a compound of the present invention and optionally one or more other agents) for a condition characterized by bacterial infection.

DETAILED DESCRIPTION OF THE INVENTION

Provided herein are compositions and methods for treating neurological disorders. In particular, provided herein are neutrophils that rescue damaged neurons, methods of making such neutrophils, and methods of promoting generation of such neutrophils in vivo.

Optic nerve crush (ONC) injury in mice is a widely used model of axonal transection. Normally, severed optic nerve axons do not regrow past the injury site. However, induction of sterile vitreal inflammation via intraocular (i.o.) injection of the fungal cell wall extract, zymosan, drives robust regeneration of retinal ganglion cell (RGC) axons in the crushed optic nerve. Curdlan (particulate β-(1,3)glucan) is the primary active ingredient in zymosan, capable of eliciting long-distance RGC axon regeneration by engaging dectin-1 (CLEC7A), a C-type lectin family member expressed on retinal microglia and eye-infiltrating myeloid cells (Proc Natl Acad Sci USA 112, 2581-2586 (2015)). Experiments described herein (FIGS. 1-11) demonstrated that a novel subset of immature Ly6G$^{low}$CD14+ neutrophils directly induces the regeneration of RGC axons, both in vitro and in vivo. Conditioned media from cultures of Ly6G$^{low}$CD14+ neutrophils enhances neurite outgrowth of explanted RGC. Heat shock abrogates the pro-regenerative properties of the neutrophil conditioned media, showing that the active ingredient is a protein. In was further demonstrated that neutrophils expressing high levels of arginase and IL-4R accumulate in the CNS at the time of EAE remission.

Accordingly, provided herein are compositions and methods for treating neurological and optical disorders. In some embodiments, methods comprise the use of Ly6G$^{low}$CD14$^+$ neutrophils, agents that induce differentiation/generation of such neutrophils in vivo, or agents secreted by such neutrophils (e.g., one or more of NGF, IGF-1, or TGFβ). In some embodiments, the Ly6G$^{low}$CD14$^+$ neutrophils are human or non-human.

The present disclosure is not limited to methods of generating Ly6G$^{low}$CD14$^+$ neutrophils in vitro or ex vivo. In some embodiments, Ly6G$^{low}$CD14$^+$ neutrophils are generated ex vivo. For example, in some embodiments, the Ly6G$^{low}$CD14$^+$ neutrophils are mobilized as immature neutrophils from bone marrow mature (e.g., by administering G-CSF to a subject) and differentiated in vitro. In some embodiments, differentiating in vitro comprising contacting neutrophils with TGFβ, curdlan, and/or HIF-1α stabilizing agents. In some embodiments, the stabilizing agent is a prolyl hydroxylase inhibitor. In some embodiments, ex vivo generated neutrophils are used in autologous or heterologous therapy or in research.

In some embodiments, Ly6G$^{low}$CD14$^+$ neutrophils are generated in vitro (e.g., from stem cells or other pluripotent cells), for example, using the differentiation method described above.

In some embodiments, Ly6G$^{low}$CD14$^+$ neutrophils are generated in vivo by administering an agent that induces differentiation of bone marrow or circulating neutrophils into Ly6G$^{low}$CD14$^+$ neutrophils.

In some embodiments, agents secreted by Ly6G$^{low}$CD14$^+$ neutrophils are utilized in therapy. In some embodiments, such agents are identified (e.g., from conditioned media that Ly6G$^{low}$CD14$^+$ neutrophils have been cultured in). In some embodiments, conditioned media is fractionated and fractions that promote neuron growth are analyzed to determine potential active components (e.g., using the assays described herein). In some embodiments, gene expression profiles of Ly6G$^{low}$CD14$^+$ neutrophils are compared to non-active neutrophils to identify genes that are unregulated in Ly6G$^{low}$CD14$^+$ neutrophils.

In some embodiments, Ly6G$^{low}$CD14$^+$ neutrophils described herein are utilized in methods or treating or preventing a neurological disorder. In some embodiments, method results in one or more outcomes selected from, for example, axonal regeneration, neurite outgrowth, or regeneration of severed axons. In some embodiments, the administering induces expression of a factor selected from, for example, G-CSF, IL-6, CXCL10, CCL2, or VEGFα.

In some embodiments, the administering comprises administering locally to an area affected by the neurological disorder (e.g., the eye, the spinal cord, the CNS, or the brain). In some embodiments, the administering comprises systemic administration. The present disclosure is not limited to particular neurological disorders. Examples include, but are not limited to, multiple sclerosis, spinal cord injury, traumatic spinal cord injury, neurodegenerative disease (e.g., Alzheimer's disease), optic neuritis, ALS, traumatic brain injury, central nervous system infection, or severe head trauma.

In yet other embodiments, the present disclosure provides a composition, kit, or system, comprising: a plurality of isolated or enriched Ly6G$^{low}$CD14$^+$ neutrophils. In some embodiments, the composition, kit, or system further comprises a pharmaceutically acceptable carrier.

The pharmaceutical compositions of the present disclosure may be administered in a number of ways depending upon whether local or systemic treatment is desired and upon the area to be treated. Parenteral administration includes intravenous, intraarterial, subcutaneous, intraperitoneal or intramuscular injection or infusion; or intracranial, e.g., intrathecal or intraventricular, administration.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

The pharmaceutical formulations of the present disclosure, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

The compositions of the present disclosure may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present disclosure, such as dyes, flavoring agents, preservatives, antioxidants, opacifiers, thickening agents and stabilizers. However, such materials, when added, should not unduly interfere with the biological activities of the components of the compositions of the present disclosure. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates.

EXPERIMENTAL

Example 1

Zymosan-Induced Axonal Regeneration is Dependent Upon Dectin-1 Expression by Retina-Resident and Hematopoietic Cells.

Zymosan is a complex mixture of molecules, many of which bind pattern recognition receptors (PRRs) on immune cells. In a recent publication curdlan (particulate β-(1,3) glucan) was identified as the primary active ingredient in zymosan, capable of eliciting long-distance RGC axon regeneration by a dectin-1 (CLEC7A) dependent pathway. Dectin-1, a C-type lectin family member and PRR, is expressed on innate immune cells and facilitates immune responses against fungi and mycobacteria. Intraocular injection of curdlan into wild-type (WT), but not dectin-1−/− mice, promotes optic nerve axon regeneration comparable to i.o. zymosan. Curdlan-elicited axonal regeneration is partially dependent on the downstream mediator CARD-9. Studies with dectin-1−/−/WT reciprocal bone marrow chimeric mice revealed a requirement for dectin-1 on both radioresistant retina-resident cells and radiosensitive hematopoietic cells for optimal RGC axonal regrowth in response to i.o. curdlan. The only retinal cells found to express dectin-1 during homeostasis are microglia and resident dendritic cells. Microglia upregulate dectin-1 above baseline levels in response to ONC injury alone. A direct role of retinal microglia in RGC axonal regeneration in our model is supported by the fact that they efficiently phagocytose zymosan particles in vivo.

Neutrophils are Prominent in Zymosan-Elicited Intraocular Infiltrates.

It was reported that i.o. zymosan injections are effective at inducing axonal regeneration when administered the day of ONC or up to 3 days later, but are ineffective beyond that time window. This indicates that the inflammatory cells that infiltrate the eye within the first 3 days post ONC play a critical role in stimulating nerve regrowth. Inflammatory cells were collected from the eyes of mice on a daily basis following i.o. zymosan injection and their subset composition analyzed by flow cytometry. A large number of CD11b+ Ly6G+ neutrophils, and smaller number of CD11b+Ly6G− monocytes/macrophages, were detected in the vitreous fluid at early time points, peaking at 1-2 days post-injection. B cells, T cells and DCs were also detected, but they compromised a minor population of the infiltrating cells. Neutrophils remained the dominant leukocyte subset until 7 days post-injection, when they became equal in number to monocytes. Monocytes, neutrophils and DCs, but not lymphocytes, expressed dectin-1. Similar results were obtained when mice were injected i.o. with curdlan.

Axonal Regeneration Correlates with the Frequency of a Novel Subset of Ly6G$^{low}$ CD14$^{hi}$ Neutrophils that Infiltrate the Vitreous.

Figure 1:
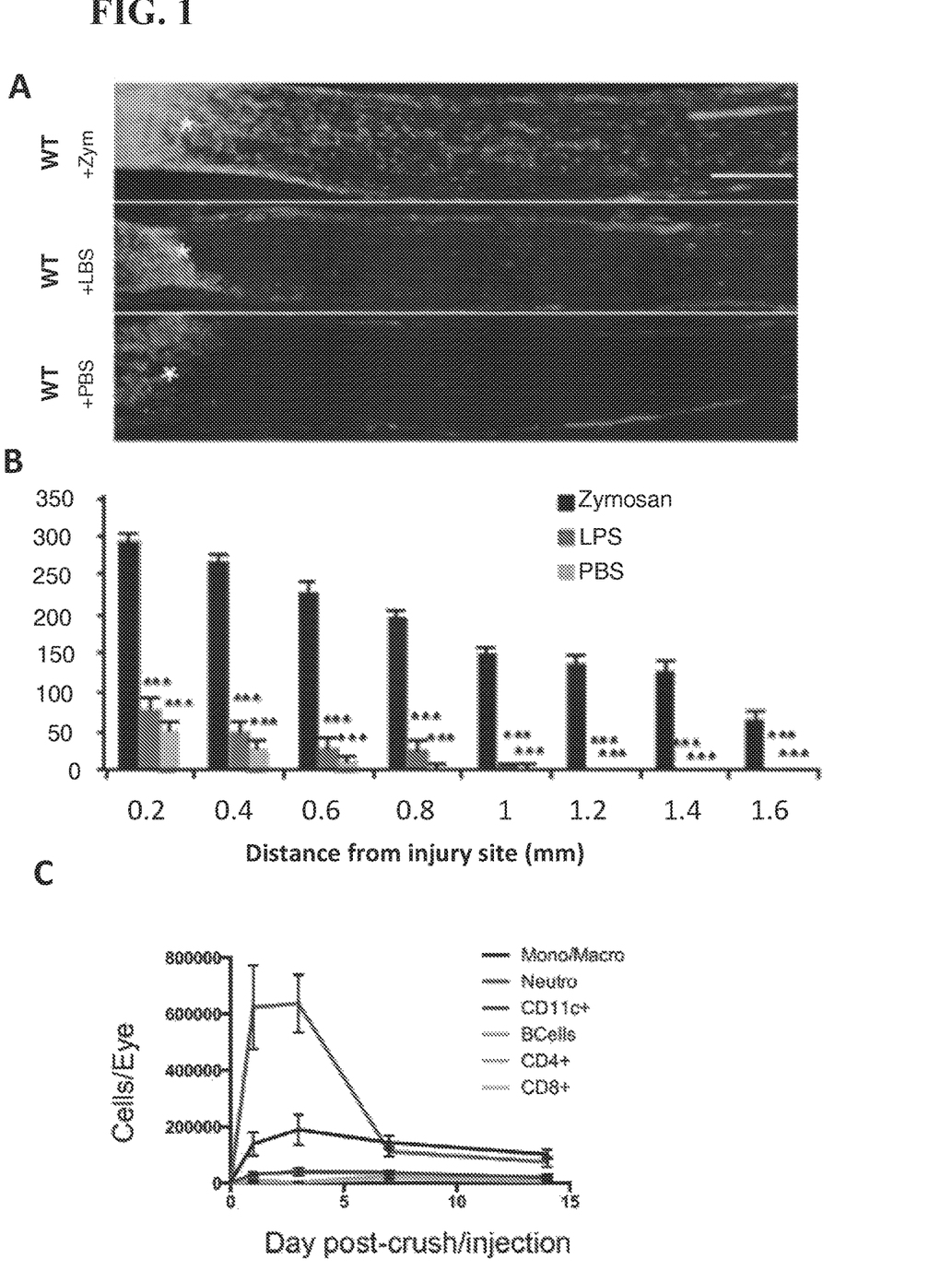
FIG. 1 shows that intraocular injection of zymosan following optic nerve crush injury (ONC) induces vitreal inflammation associated with axonal regrowth. (A) Longitudinal sections of optic nerves harvested from adult C57BL/6 mice 2 weeks post-ONC and i.o. injection of either Zymosan, LPS, or PBS. (B) Quantitation of axon density at serial distances from the injury site. (n=7-9 nerves/group) (C) Flow cytometric analysis of i.o. inflammatory infiltrates at serial time points post-ONC and i.o. zymosan injection.
Figure 2:
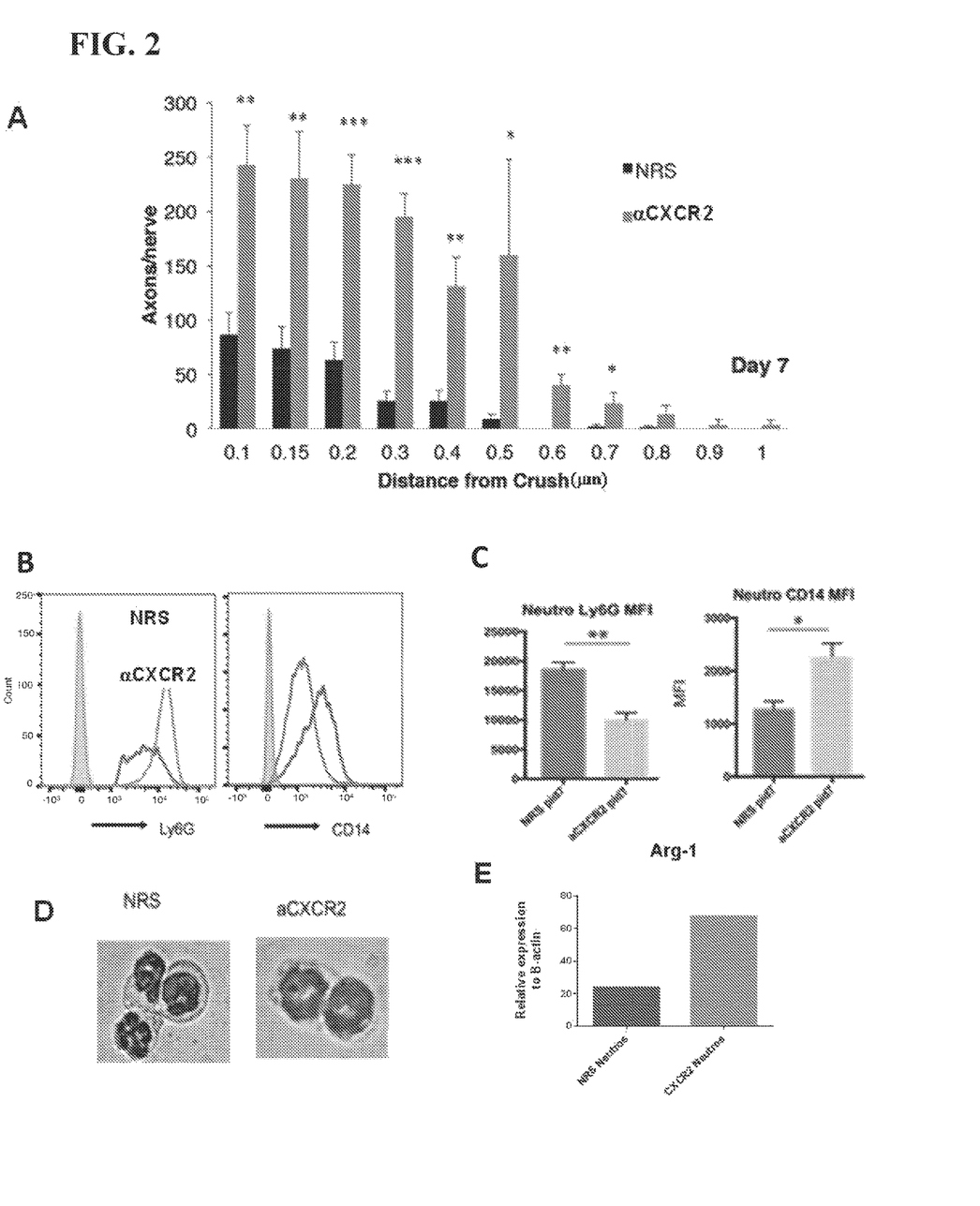
FIG. 2 shows blockade of the chemokine receptor, CXCR2, in mice subjected to i.o. zymosan and ONC, skews eye-infiltrating neutrophils towards a novel Ly6G$^{low}$CD14+ subset and enhances axonal regeneration. (A) Optic nerves were harvested on day 7, fixed and stained with an antibody specific for GAP43. (B,C) Expression of Ly6G and CD14 on infiltrating neutrophils, measured by flow cytometry. (B) Representative histograms. (C) Mean fluorescent intensity (MFI), averaged over 7 mice per group. (D, E) CD45$^{hi}$CD11b+ Ly6G$^{hi}$ (left) and Ly6G$^{low}$(right) neutrophils were FACS sorted from the vitreal infiltrates of mice treated with i.o. zymosan and NRS or αCXCR2, respectively. (D) Representative cytospins. (E) Arginase transcripts were measured by qRT-PCR *p<0.05, **p<0.01

Migration of neutrophils to the eye following i.o. zymosan injection correlates with upregulation of CXCL2, a prominent chemoattractant for neutrophils, in the vitreous. To determine the importance of neutrophils in i.o. zymosan-elicited axonal regeneration, their entry into the eye was blocked by intraperitoneal (i.p.) treatment with antisera to CXCR2, the only receptor for CXCL2 in mice. Unexpectedly, mice treated with anti-CXCR2 (αCXCR2) exhibited more robust axonal regeneration than mice treated with control sera. In fact, by day 14 RGC axons had regrown so profusely in the αCXCR2 treated group that we had to harvest optic nerves on day 7 (i.e. one week earlier than usual) in order to be able to count them (FIG. 2). Flow cytometric analysis of intraocular infiltrates revealed that, rather than depleting neutrophils from the vitreous, αCXCR2 treatment actually resulted in enrichment of a subset of Ly6G$^{low}$ neutrophils (FIG. 2). The percentage of Ly6G$^{low}$ cells among intraocular, as well as circulating, neutrophils was 2-3 fold higher in mice treated with αCXCR2 compared with mice treated with control sera. These neutrophils universally upregulated CD14, a marker that is most commonly associated with macrophages (FIG. 2). A significant percent expressed CD115, another myeloid marker, and CD244, a SLAM family receptor. CD244 has been detected on alternatively activated myeloid cells in other experimental systems. The Ly6G$^{low}$ subset was also distinguished by expression of the chemokine receptor, CCR2 (FIG. 2). Ly6G$^{low}$ neutrophils, harvested either from the eyes or blood of αCXCR2 treated mice, had a ring-form nucleus consistent with an immature phenotype, while Ly6G$^{hi}$ neutrophils, harvested from mice treated with control sera, bore a multi-lobulated nucleus (FIG. 2).

Adoptive Transfer of Ly6G$^{low}$ CD14$^{hi}$ Neutrophils into the Eyes of Mice with ONC Promotes RGC Survival and Induces Axonal Regeneration.

Figure 3:
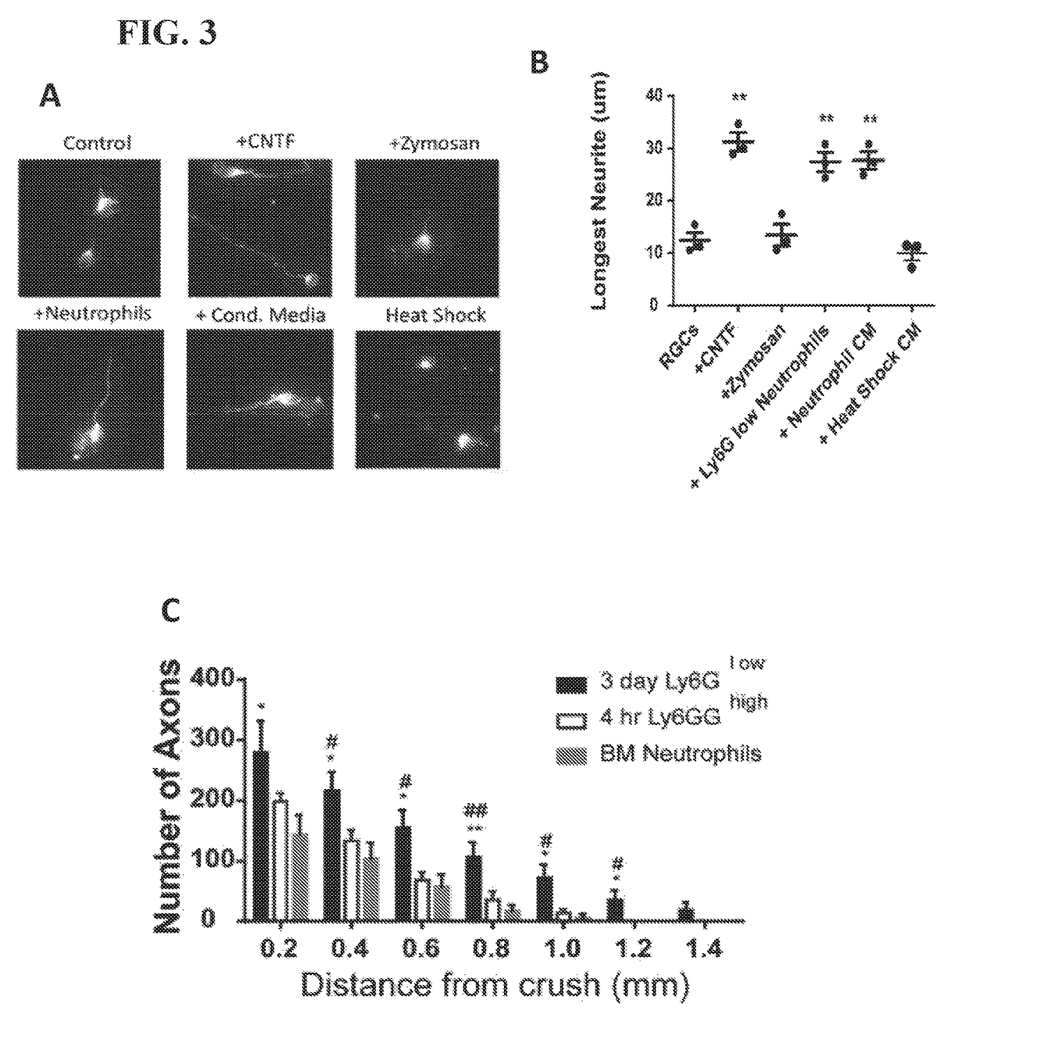
FIG. 3 shows that zymosan induced Ly6G$^{low}$ CD14+ neutrophils directly promote retinal ganglion cell (RGC) neurite outgrowth in vitro and in vivo. (A) Representative images of RGCs cultured under the indicated conditions. (B) The average length of the longest neurite was determined for each group. *p<0.05, **p<0.01 compared to RGCs. (C) Axonal densities of zymosan-elicited i.p. Ly6G$^{low}$ CD14+ neutrophils or conventional Ly6G$^{hi}$ neutrophils, or nave bone marrow (BM) neutrophils that were adoptively transferred into the eyes of mice on the day of ONC and 3 days later (10$^6$ cells/eye/dose). (n=6-8 nerves/group). * (compared to PBS), # (compared to Ly6G$^{high}$ neutrophils) p<0.05, **, ##p<0.01

It was found that zymosan elicited Ly6G$^{low}$CD14$^{hi}$ neutrophils induce neurite outgrowth of purified RGCs in vitro (FIG. 3). In order to assess their neuroprotective and pro-regenerative properties in vivo, those cells were transferred into the eyes of mice with ONC injury. It is technically not feasible to obtain a sufficient number of neutrophils from the eyes of mice injected with i.o. zymosan for adoptive transfer experiments. As an alternative, neutrophils were harvested from the peritoneal cavity of mice 3 days following intraperitoneal (i.p.) injection of zymosan. The majority of cells isolated from peritoneal lavages on day 3 resemble the immature Ly6G$^{low}$ CD14$^{hi}$ neutrophils isolated from the eyes of mice subjected to ONC with i.o. zymosan and αCXCR2 treatment, with respect to the cell surface phenotype that these cells are Ly6G$^{low}$, CD14+, and have a ring form nuclear morphology. Mice were injected i.o. with i.p. zymosan elicited Ly6G$^{low}$ neutrophils, i.p. thioglycolate Ly6G$^{hi}$ neutrophils, nave bone marrow neutrophils, or PBS as additional control conditions on the day of ONC injury and 3 days later. In these experiments, TLR2−/−; dectin1−/− double knockout (DKO) mice were used as adoptive transfer recipients in order to eliminate the possibility that small amounts of zymosan contamination the inoculum, or released by donor neutrophils into the vitreous, could affect the outcome. All mice were euthanized on day 14 to harvest retina and optic nerves. Ly6G$^{low}$ neutrophils induced significantly more regeneration of transected RGC axons compared to Ly6G$^{hi}$ neutrophils, bone marrow neutrophils, or PBS (FIG. 3). Furthermore, RGC survival was significantly increased in mice injected with Ly6G$^{low}$ neutrophils, indicative of a neuroprotective effect.

Growth Factors, Cytokines and Chemokines are Secreted into the Vitreous in Response to ONC/i.o. Zymosan.

Figure 4:
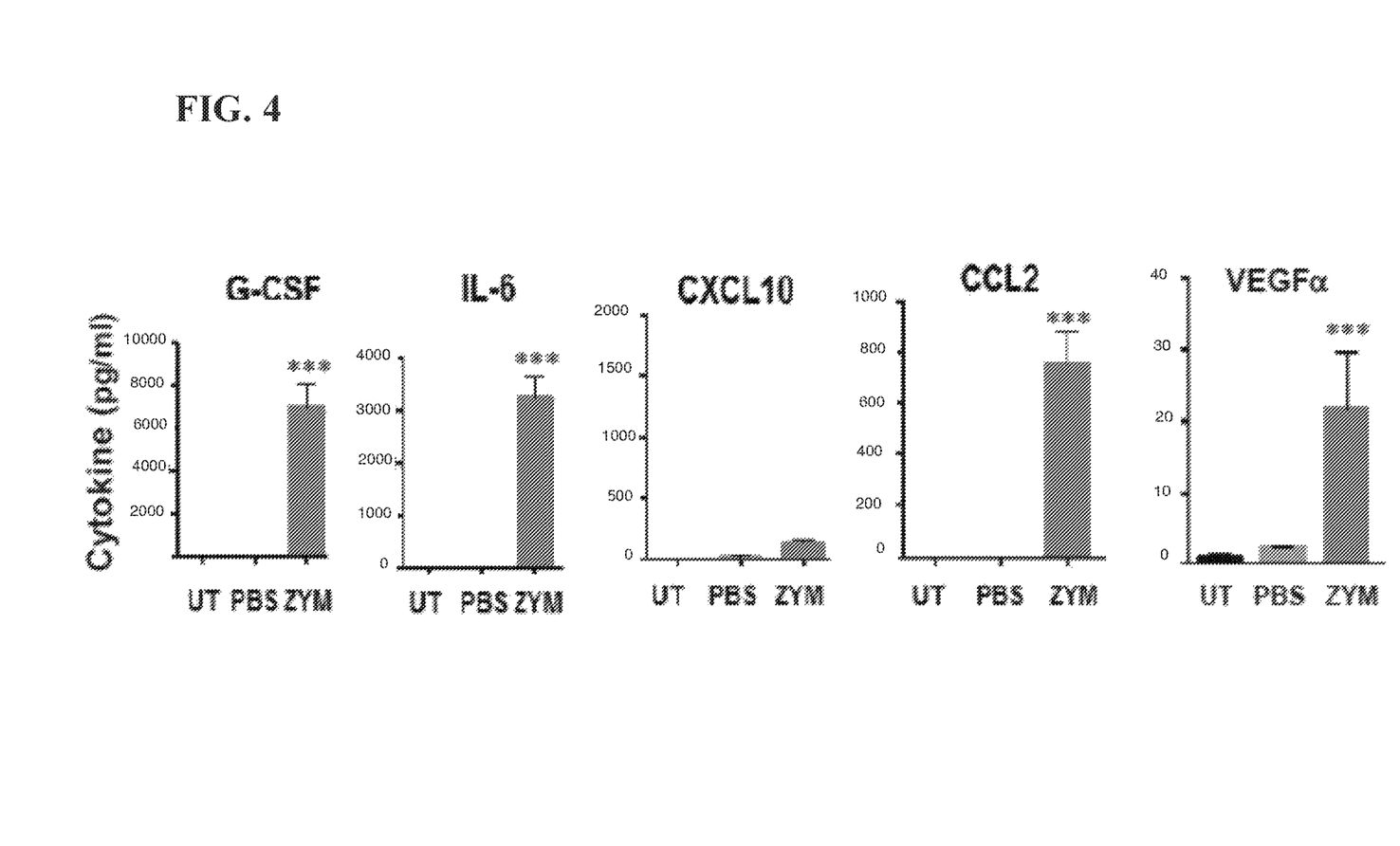
FIG. 4 shows factors upregulated in the eyes of mice in response to ONC and i.o. zymosan.

It was next interrogated the inflammatory milieu of the vitreous following ONC/i.o. zymosan injection. It was found that the CC chemokine CCL2 was upregulated, whereas as other chemokines, such as CXCL10, were not (FIG. 4). Ly6GlowCD14+ neutrophils express CCR2, the cognate receptor for CCL2 (FIG. 2). Therefore, they are likely to migrate towards intraocular CCL2. In addition to CCL2, granulocyte colony stimulating factor (G-CSF), IL-6 and VEGFα were elevated in the eyes of actively treated mice compared to untreated mice or mice injected i.o. with PBS (FIG. 4). Expression of CCL2, G-CSF and IL-6 was further enhanced by systemic treatment with αCXCR2 antisera. Collectively, these data led to the hypothesis that CCL2, G-CSF and IL-6 act synergistically to orchestrate Ly6G$^{low}$CD14+ neutrophil trafficking from the circulation to the eye.

Ly6G$^{low}$ CD14$^{hi}$ Neutrophils Secrete Growth Factors that Stimulate Axon Regeneration In Vitro and In Vivo.

Figure 5:
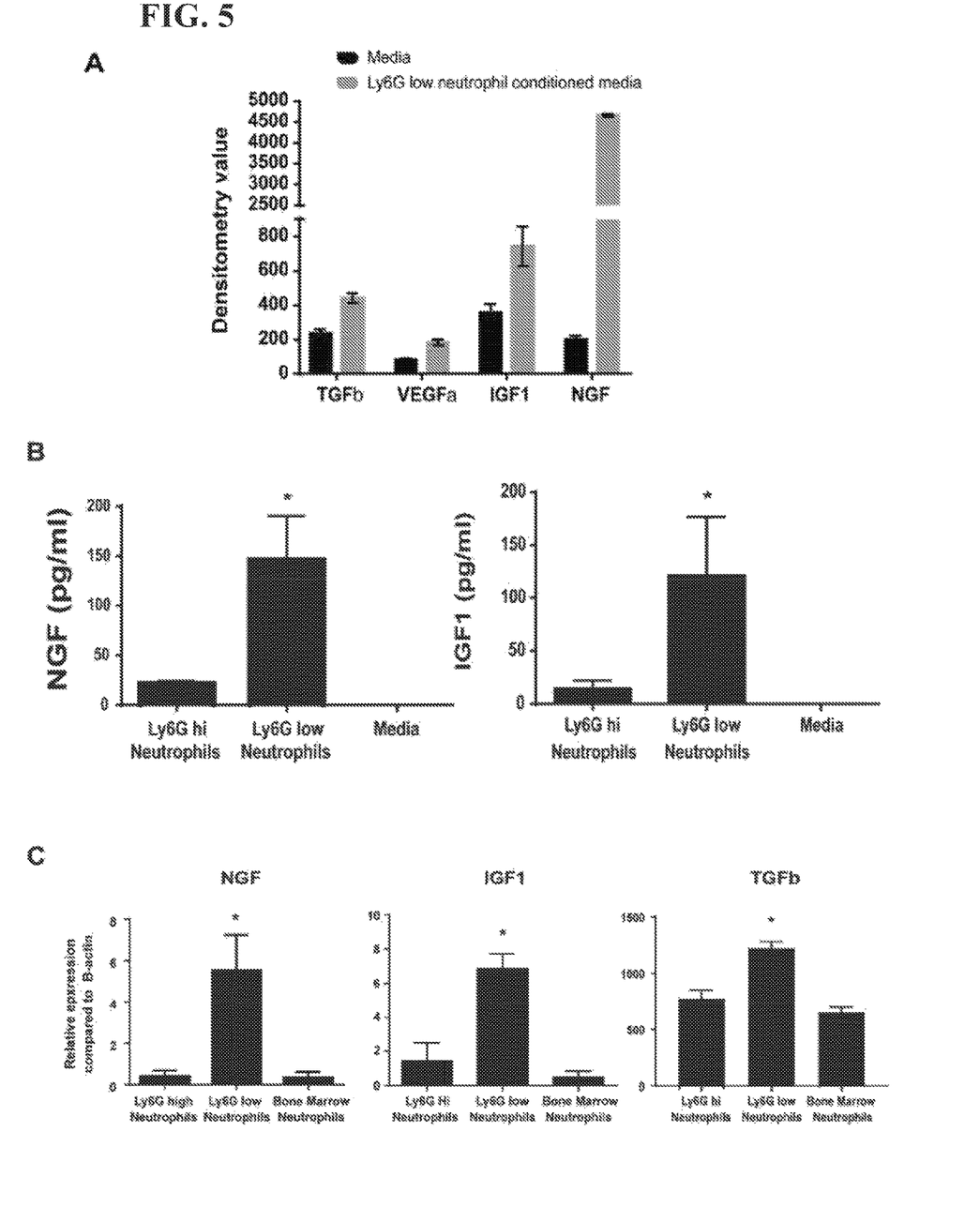
FIG. 5 shows that zymosan induced Ly6G$^{low}$ CD14+ neutrophils secrete neuroprotective growth factors. (A) An array of proteins were detected in the conditioned media (CM) of i.p. zymosan elicited Ly6G$^{low}$ neutrophils (grey bars), or in unconditioned media (black bars,) using an immunoblot assay. NGF and IGF1, and TGF were expressed at relatively high levels in the CM of Ly6G$^{low}$. (B) NGF and IGF1 protein levels were corroborated by ELISA. (C) IGF1, NGF, and TGFβ transcript levels were measured in RNA extracted from Ly6G$^{low}$ pro-regenerative neutrophils, Ly6G$^{high}$ conventional neutrophils, or nave bone marrow neutrophils via quantitative RT-PCR *p<0.05.
Figure 6:
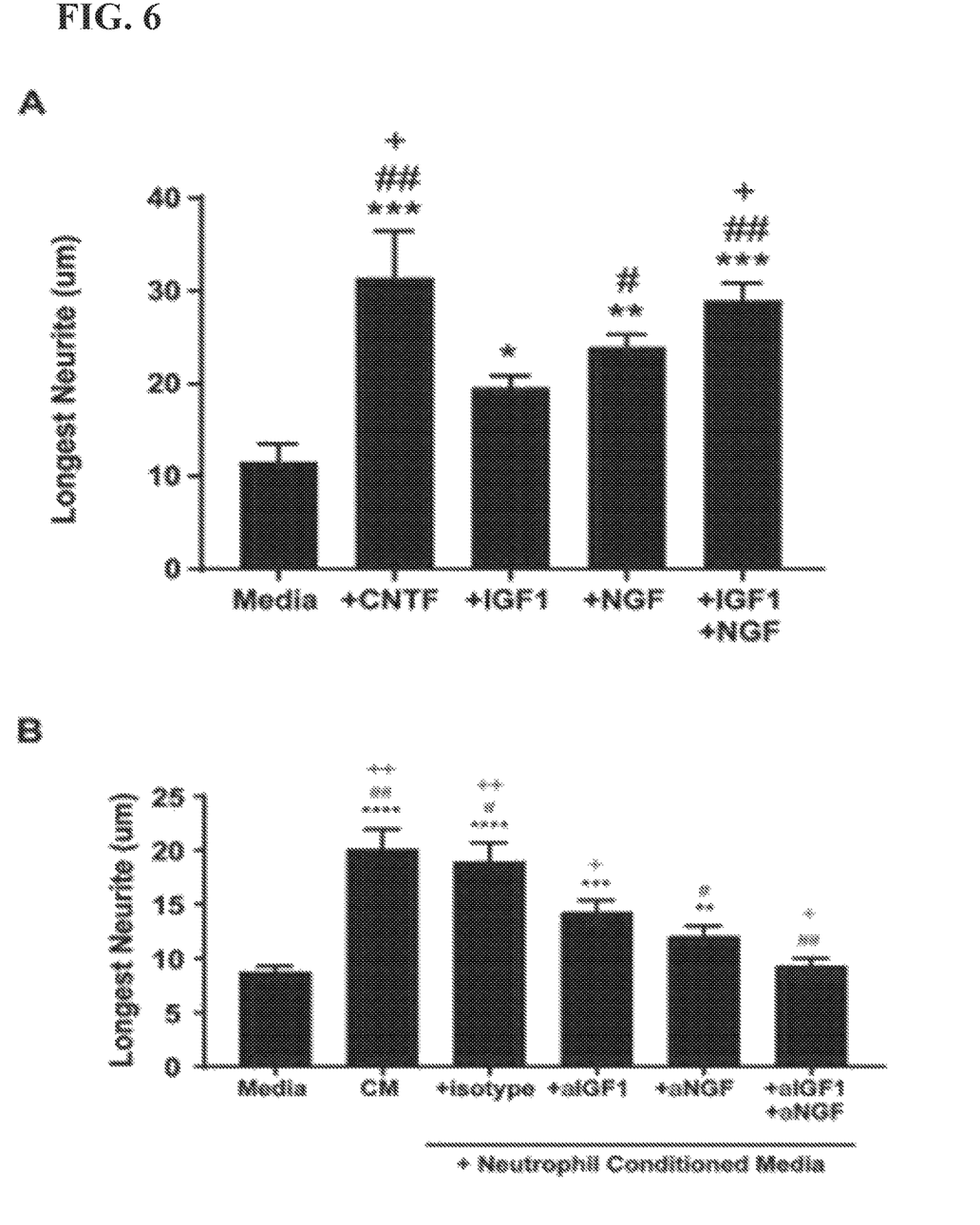
FIG. 6 shows that recombinant NGF1 and IGF1 have an additive effect in promoting RGC neurite outgrowth. Conversely, neutralization of IGF1 and NGF1 abrogate the pro-regenerative properties of LY6G$^{low}$ neutrophil-conditioned media. (A) The combination of IGF1 and NGF was more effective in enhancing neurite outgrowth than either factor in isolation (n=100 neurons in each group). (B) Administration of neutralizing antibodies against both NGF and IGF-1 was most effective in blocking the enhancement of neurite outgrowth mediated by Ly6G$^{low}$ neutrophil-conditioned media (n=100 neurons in each group). *p<0.05, p<0.01 *p<0.001 compared to media. #p<0.05, ##p<0.01 compared to IGF1.+p<0.05, ++p<0.01 compared to NGF.
Figure 7:
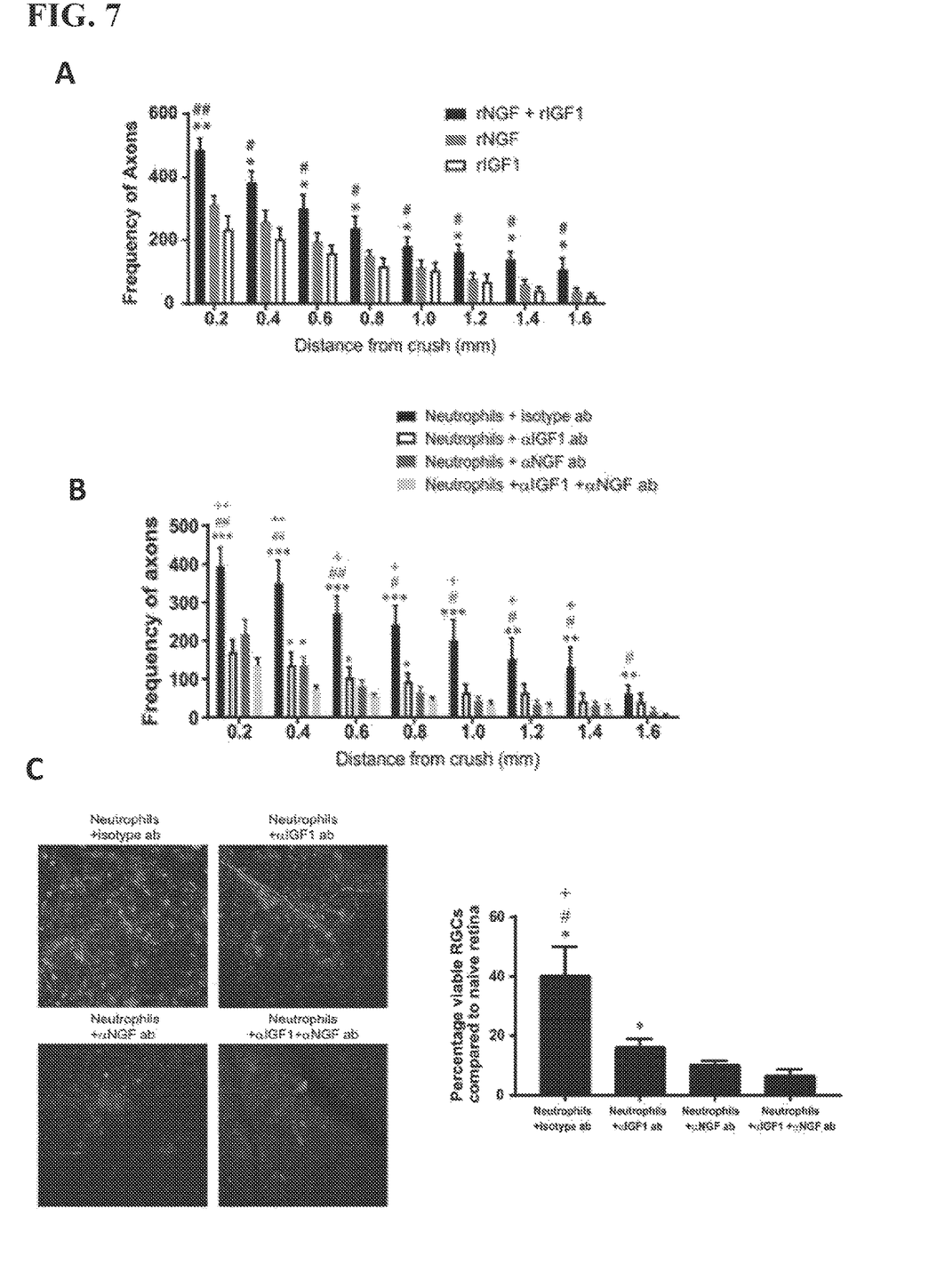

Co-culture of zymosan elicited Ly6G$^{low}$ neutrophils with RGCs stimulates axon outgrowth in vitro (FIG. 3). To determine if the mechanism of neutrophil mediated axon regeneration was direct neutrophil to neuron interaction, or a secreted factor, neutrophils were placed in RGC media. Twenty-four hours later, the cells were spun down and media removed. The neutrophil conditioned media without any neutrophils was then placed on the RGC cultures, and was able to stimulate neurite outgrowth (FIG. 3). This axon outgrowth was inhibited by heatshock of the media (FIG. 3). A growth factor array of the neutrophil conditioned media identified that the neutrophils secreted multiple growth factors including nerve growth factor (NGF), insulin like growth factor-1 (IGF1), vascular endothelial growth factor-alpha (VEGFα), and transforming growth factor-beta (TGFβ). RT-PCR confirmed elevated transcription of these factors. ELISA confirmed elevated protein levels of NGF and IGF1 by Ly6G$^{low}$ neutrophils (FIG. 5). Culture of RGCs with recombinant IGF1 or NGF stimulates neurite outgrowth in vitro. The pro-growth effect of either IGF1 or NGF is synergistic when the two growth factors are combined together in vitro producing better RGC outgrowth than a single growth factor alone (FIG. 6). To determine if these growth factors are sufficient to drive axon regeneration, recombinant IGF1 or NGF alone, or rIGF1+rNGF in combination was directly injected into the vitreal fluid of mice that had undergone ONC on the day of ONC and again 3 days later. This results in RGC axon regeneration 14 days after ONC. RGC axon regeneration is most significant in mice that have received both recombinant NGF and IGF1 in combination (FIG. 7). To determine the importance of IGF1 and NGF production by Ly6G$^{low}$ neutrophils in stimulating RGC axon regeneration, Ly6G$^{low}$ zymosan elicited i.p. neutrophils were collected, purified, and adoptively transferred i.o. with either anti-IGF1 antibody, anti-NGF antibody, or both anti-IGF1 and anti-IGF1 antibody together at the time of ONC, and again 3 days after ONC. One group included Ly6G$^{low}$ neutrophils and isotype control antibody adoptively transferred to determine if there was a nonspecific antibody effect on axon regeneration. PBS i.o. was an additional control. Adoptive transfer of Ly6G$^{low}$ antibodies with either anti-IGF1 or anti-NGF antibodies decreased the amount of axon regeneration. Adoptive transfer of Ly6G$^{low}$ neutrophils with antibodies that neutralize both IGF1 and NGF most reduced the number of axons that regenerated (FIG. 7). Furthermore, retinal whole mount examination showed that RGC survival as determined by brn3a immunohistochemistry was significantly decreased in mice injected with Ly6G$^{low}$ neutrophils with either IGF1, NGF, or both IGF1 and NGF neutralizing antibodies indicating that blocking IGF1 and/or NGF decreases the Ly6G$^{low}$ neutrophil's neuroprotective effect.

Figure 8:
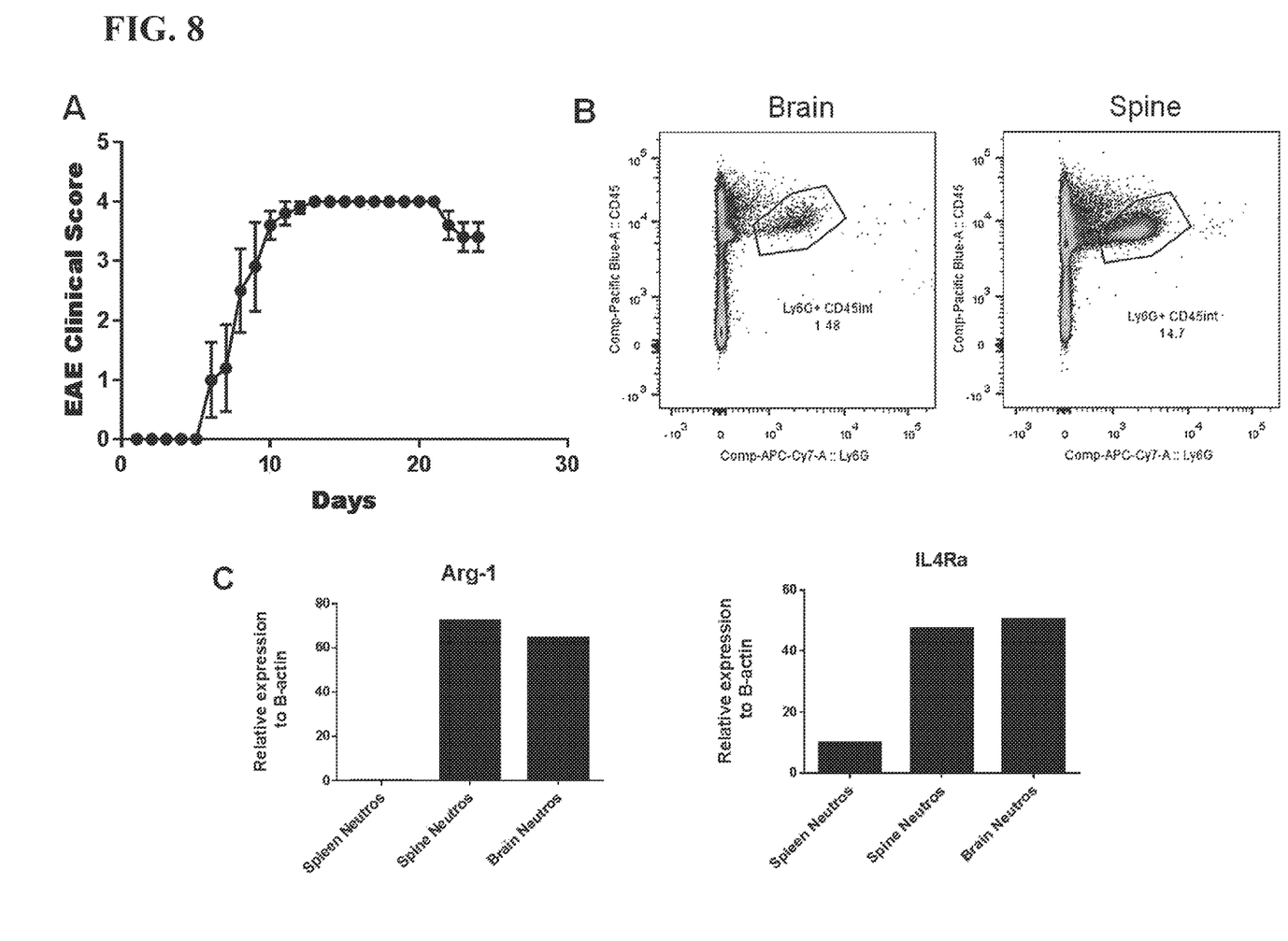
FIG. 8 shows that neutrophils with characteristics of the pro-regenerative phenotype accumulate in the CNS at the time of EAE remission. (A) Clinical course of mice injected with MOG-specific Th17 cells. n=5 (B) The mice were euthanized on day 25 post-transfer, as they were beginning to recover function, and CNS mononuclear cells were isolated for flow cytometric analysis.

Ly6G$^{low}$ Neutrophils are Associated with Remission in a Mouse Model of Multiple Sclerosis Ly6G$^{low}$ neutrophils were identified in the CNS tissue of mice that have had experimental autoimmune encephalitis (EAE), a mouse model of multiple sclerosis at the time of remission. The mice present with an ascending paralysis and demyelination in the spinal cord and brain on pathology. Over a period of weeks, some mice are able to slowly improve, and during this remission, Ly6G$^{low}$ neutrophils can be found in the CNS. These neutrophils have ringed nuclei on morphology, and express high levels of arginase 1 and IL4-receptor transcripts, similar to the pro-regenerative Ly6G$^{low}$ neutrophils (FIG. 8).

Ly6G$^{low}$ CD14$^{hi}$ Neutrophils are Associated with the Regeneration of Severed Axons in the Spinal Cord.

Figure 9:
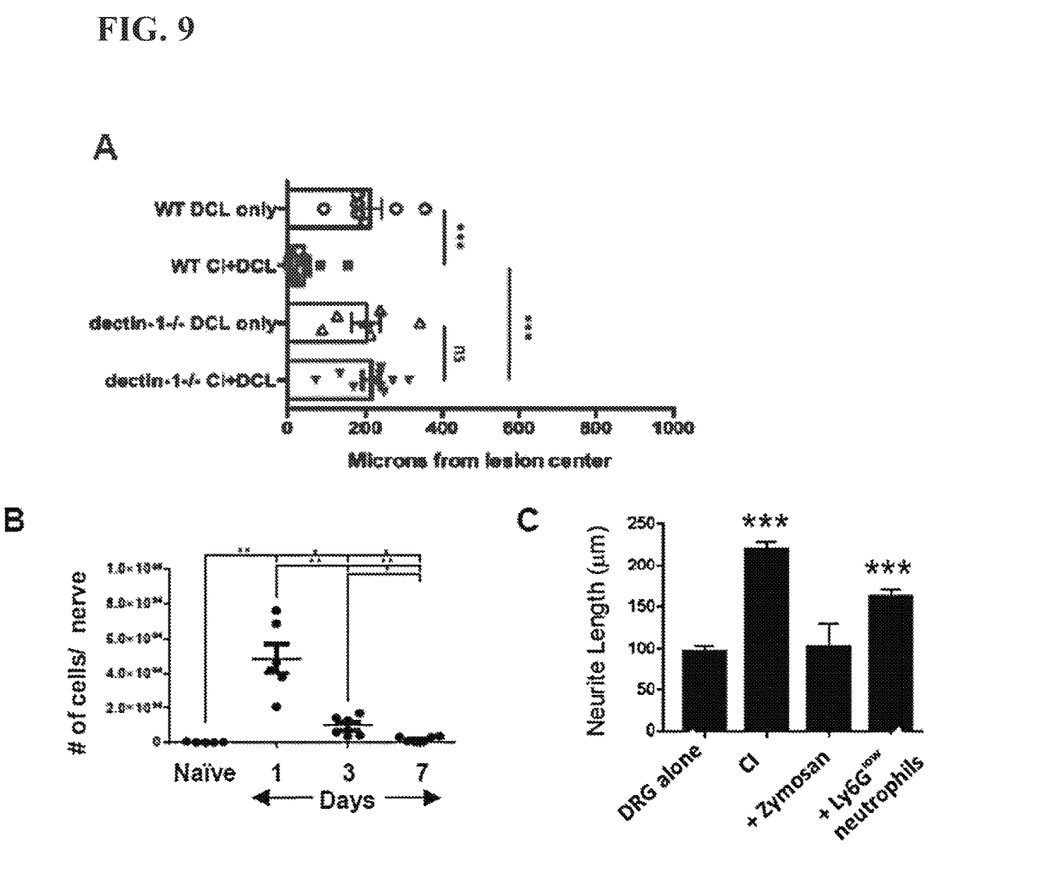
FIG. 9 shows that Ly6G$^{low}$ neutrophils correlate with sensory axonal outgrowth. (A) C57BL/6 WT or dectin-1 knock-out (−/−) mice were subjected to bilateral dorsal column laceration (DCL) at T6 or sham surgery and euthanized 5 weeks later. (B) Sciatic nerves were crushed with forceps at mid-thigh level, and dissected on day 1, 3 or 7 post-injury. (C) DRG neurons were dissected from nave adult C57BL/6 mice and cultured with media alone (negative control), zymosan (at 100 µg/ml), or zymosan-elicited Ly6Glow i.p. neutrophils. For a positive control, DRG were harvested from another group of mice 1 week following CI.

Regrowth of sensory axons following dorsal column transection is boosted by inflicting a conditioning crush injury (CI) to the sciatic nerve 1-2 weeks earlier. It was found that, similar to zymosan-induced RGC regeneration, CI-enhanced spinal axon regeneration is impaired in mice that are deficient in the myeloid cell receptor, dectin-1 (FIG. 9A). This implies that CI leads to the release of an endogenous dectin-1 ligand, which has yet to be identified. CI induced axon regeneration correlated with infiltration of the crushed sciatic nerve by dectin-1+Ly6G$^{low}$CD14+ neutrophils (FIG. 9B). Consistent with these results, zymosan-elicited Ly6G$^{low}$CD14+ neutrophils induced significant neurite outgrowth of dissociated dorsal root ganglia neurons, while conventional Ly6G$^{11}$ bone marrow neutrophils had no effect (FIG. 9C). Collectively, the data are consistent with the hypothesis that N2-like neutrophils play a reparative role following trauma to different regions of the CNS, including the spinal cord.

Figure 10:
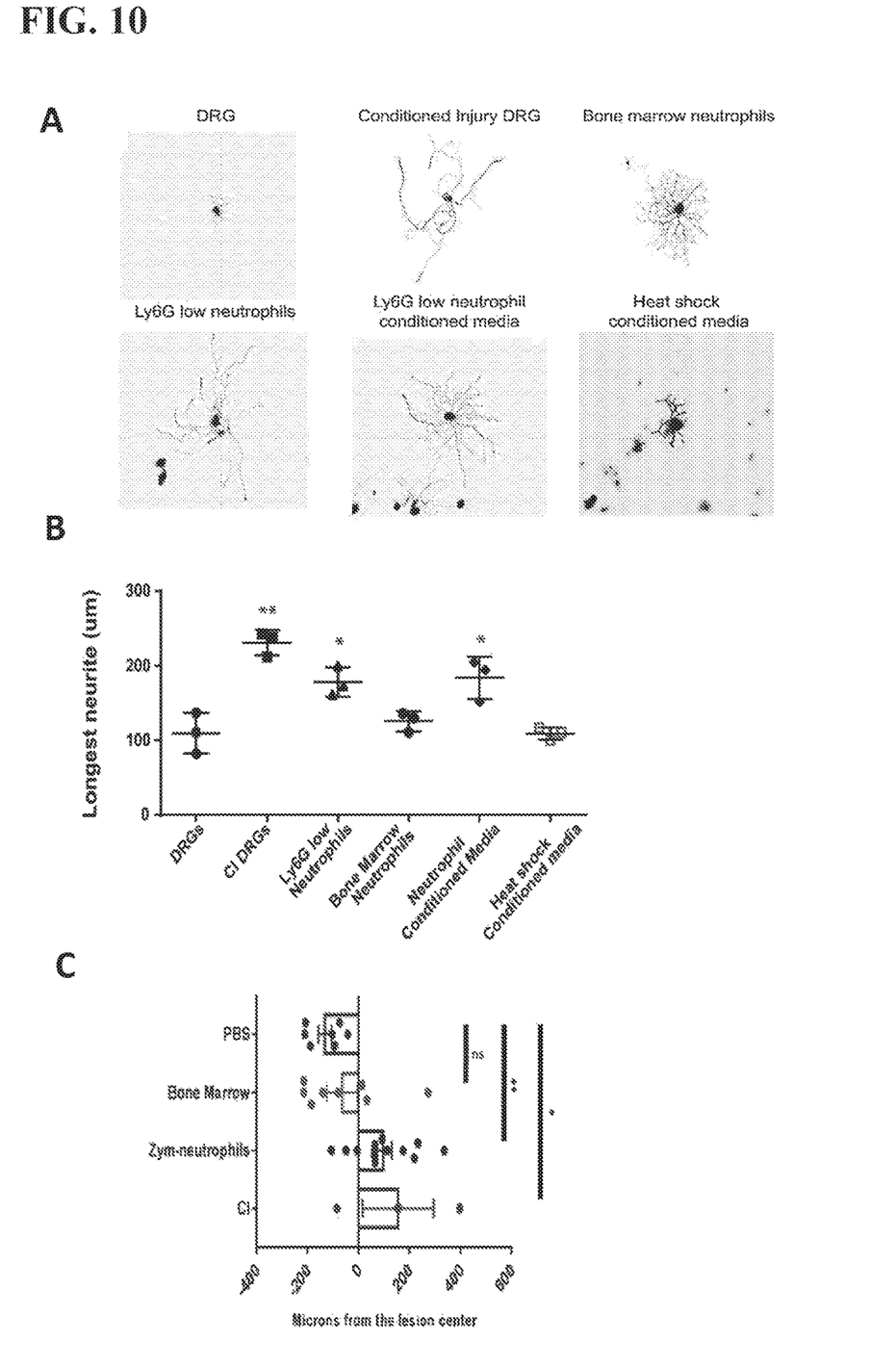
FIG. 10 shows that zymosan elicited Ly6G$^{low}$ neutrophils promote the outgrowth of spinal cord dorsal root ganglion axons both in vitro and in vivo (A) Representative images of DRGs cultured under the indicated conditions. (B) Average neurite length of DRGs cultured with Ly6G$^{low}$ neutrophils or their conditioned media. (n=3 experiments of 50 axons quantified in each group) *p<0.05, **p<0.01 compared to DRGs. (C) Transfer of the zymosan-elicited Ly6G$^{low}$ neutrophils, but not nave bone marrow neutrophils, enhanced regeneration of the severed spinal cord axons (n=3-12 mice). *p<0.05, **p<0.01

Ly6G$^{low}$ CD14$^{hi}$ Neutrophils are Able to Stimulate Axon Regeneration of Severed Axons in the Spinal Cord It was found that the pro-regenerative effect of the Ly6G$^{low}$ neutrophils can be applied to other CNS neuron systems, including spinal cord neurons. Ly6G$^{low}$ neutrophils were co-cultured with dorsal root ganglion cell (DRGs) in vitro. Similar to the interaction between Ly6G$^{low}$ neutrophils and RGCs, Ly6G$^{low}$ neutrophils can stimulate DRG axon outgrowth both directly in co-culture together, or through Ly6G$^{low}$ neutrophil condition media after neutrophils removed from the culture media. The conditioned media loses its pro-axon growth effect when heat shocked (FIG. 10). In a mouse model of spinal cord injury, the dorsal spinal cord transection, adoptive transfer of zymosan stimulated Ly6G$^{low}$ CD14+ neutrophils into DRGs after thoracic dorsal spinal cord transection stimulated dorsal spinal column axons to regenerate across the transection in mice (FIG. 10). Adoptive transfer of bone marrow neutrophils did not induce axon growth across the spinal cord transection. An additional control of PBS injection into the DRG after spinal cord transection also does not induce axon growth.

Figure 11:
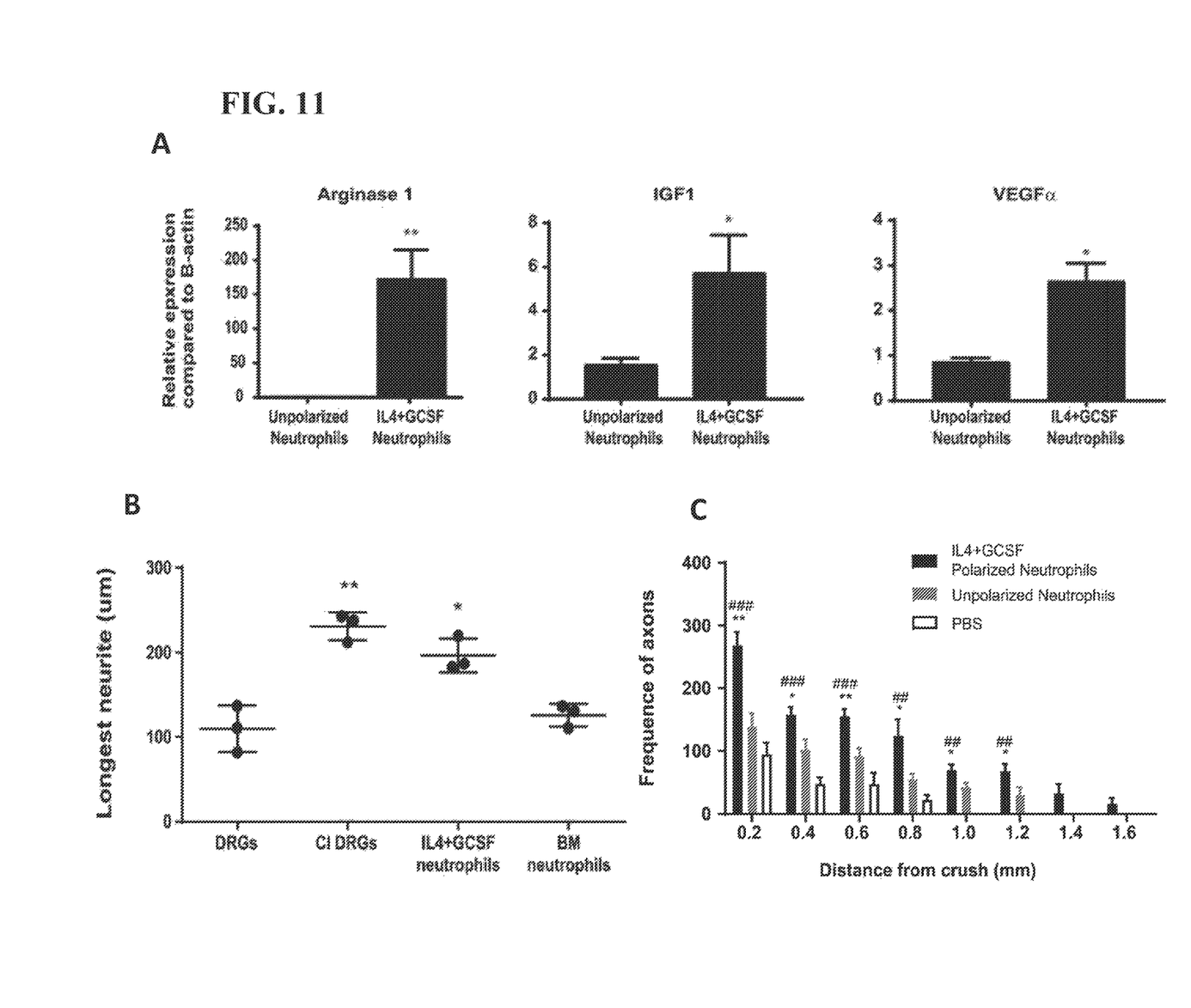
FIG. 11 shows that polarization of nave bone marrow neutrophils with a combination of recombinant IL4 and GCSF drives their differentiation into a pro-regenerative phenotype. (A) Naïve bone marrow neutrophils cultured with a combination of IL4 and GCSF express high levels of arginase, VEGFα and IGF1 transcripts. (B)/IL-4/GCSF-polarized bone marrow neutrophils stimulate DRG neurite outgrowth in vitro (n=50 axons quantified). *p<0.05, **p<0.01 compared to DRGs (C) Adoptive transfer of IL4/GCSF polarized bone marrow neutrophils into the eyes of mice on the day of ONC and 3 days later, promotes RGC axon regeneration (n=6 nerves in each group). *p<0.05, **p<0.01 compared to unpolarized neutrophils #p<0.05, ##p<0.01 ###p<0.001 compared to PBS.

Ly6G$^{low}$ CD14$^{hi}$ Pro-Regenerative Neutrophils can be Generated De Novo Through Polarization of Nave Bone Marrow Neutrophils Examination of the vitreal fluid of mice that have undergone ONC and i.o. zymosan injection that results in axon regeneration by Ly6G$^{low}$ CD14+ neutrophils identified cytokines and growth factors that are capable of polarizing immune cells including IL4 and GCSF. Naïve bone marrow neutrophils were purified and cultured with either IL4, GCSF, or the combination of IL4 and GCSF. The combination of IL4 and GCSF polarization resulted in a Ly6G$^{low}$ CD14+ neutrophil that produced high levels of arginase 1, VEGFα, and IGF1 (FIG. 11). When co-cultured with DRGs in vitro, these IL4/GCSF polarized Ly6G$^{low}$ neutrophils stimulated DRG neurite outgrowth similar to the zymosan elicited Ly6G$^{low}$ neutrophil. To determine if the IL4/GSCF polarized neutrophil was able to stimulate axon regeneration in vivo, IL4/GCSF polarized neutrophils were adoptively transferred into the eyes of mice that had undergone ONC. Mice that received IL4/GCSF polarized neutrophils showed more axon regeneration after adoptive transfer compared to adoptive transfer with unpolarized bone marrow neutrophils (FIG. 11).

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

We claim:

1. A method of treating or preventing a neurological disorder, comprising: administering a plurality of Ly6G$^{low}$CD14$^+$ neutrophils or a secreted product thereof to a subject diagnosed with or at risk of a neurological disorder under conditions such that said neurological disorder is treated or prevented, wherein the secreted product is conditioned media harvested from cultures of said neutrophils.

2. The method of claim 1, wherein said administering results in one or more outcome selected from the group consisting of axonal regeneration, neurite outgrowth, and regeneration of severed axons.

3. The method of claim 1, wherein said administering induces expression of a factor selected from the group consisting of G-CSF, IL-6, CXCL10, CCL2, and VEGFα.

4. The method of claim 1, wherein said administering comprises administering locally to an area affected by said neurological disorder.

5. The method of claim 4, wherein said area is selected from the group consisting of the eye, the spinal cord, and the brain.

6. The method of claim 1, wherein said administering comprises systemic administration.

7. The method of claim 1, wherein said Ly6G$^{low}$CD14$^+$ neutrophils are mobilized from bone marrow mature or isolated from bone marrow as immature neutrophils and differentiated in vitro with TGFβ, curdlan, and a prolyl hydroxylase inhibitor.

8. The method of claim 1, wherein said neurological disorder is selected from the group consisting of multiple sclerosis, ALS, neurodegenerative disease, optic neuritis, spinal cord injury, traumatic spinal cord injury, Alzheimer's disease, traumatic brain injury, central nervous system infection, and severe head trauma.

9. A method of obtaining Ly6G$^{low}$CD14$^+$ neutrophils, comprising:

a) isolating immature neutrophils from a subject; and b) contacting said neutrophils with TGFβ, curdlan, and a prolyl hydroxylase inhibitor.

10. The method of claim 9, wherein said immature neutrophils are obtained from blood or bone marrow of said subject.

11. The method of claim 9, further comprising the step of administering said Ly6G$^{low}$CD14$^+$ neutrophils to a subject diagnosed with or at risk of neurological disorder.

12. The method of claim 11, wherein said subject diagnosed with or at risk of a neurological disorder is the same or a different subject than said subject that said immature neutrophils are isolated from.

13. A composition, kit, or system, comprising:

A plurality of Ly6G$^{low}$ CD14$^+$ neutrophils.

* * * * *